United States Patent [19]
Rinne et al.

[11] 4,201,204
[45] May 6, 1980

[54] BREATHING GAS HUMIDIFIER

[75] Inventors: Gerhart Rinne, Stockelsdorf; Jürgen Sachtler, Lübeck, both of Fed. Rep. of Germany

[73] Assignee: Drägerwerk Aktiengesellschaft, Fed. Rep. of Germany

[21] Appl. No.: 870,634

[22] Filed: Jan. 19, 1978

[30] Foreign Application Priority Data

Jan. 24, 1977 [DE] Fed. Rep. of Germany ....... 2702674

[51] Int. Cl.² ............................................. A61M 16/00
[52] U.S. Cl. ........................... 128/203.27; 128/204.14
[58] Field of Search .............. 128/192, 193, 186, 187, 128/188, 173.2; 261/130, 131, 142, DIG. 65

[56] References Cited

U.S. PATENT DOCUMENTS

| | | | |
|---|---|---|---|
| 3,820,540 | 6/1974 | Hirtz et al. ......................... | 128/192 X |
| 3,982,095 | 9/1976 | Robinson ........................... | 261/142 X |
| 4,051,205 | 9/1977 | Grant ................................. | 128/192 X |

FOREIGN PATENT DOCUMENTS

257247  9/1948 Switzerland ............................. 128/192
1294809 11/1972 United Kingdom ..................... 128/192

Primary Examiner—Henry J. Recla
Attorney, Agent, or Firm—McGlew and Tuttle

[57] ABSTRACT

A breathing gas humidifier for connection between a respirator and a patient, comprises a float chamber having water therein up to a predetermined level which is connected by a top connection to a mixing chamber above water level and is connected by a bottom connection to the mixing chamber below water level. A heater is in the bottom connection for keeping the water boiling in the mixing chamber. The respiratory gas is circulated through a respiratory gas line which extends through the mixer and has a discharge portion extending out of the mixer which is adapted to be connected through a mouthpiece to the patient. An overheater is provided in the circulating line discharge between the mixing chamber and the mouthpiece, in the direct vicinity of the mixing chamber, which is operated in accordance with the temperature sensed by a temperature sensor at the mouthpiece connection to the patient to a desired final temperature before it is delivered to the patient.

2 Claims, 2 Drawing Figures

BREATHING GAS HUMIDIFIER

FIELD AND BACKGROUND OF THE INVENTION

This invention relates to respirators in general and, in particular, to a new and useful gas humidifier for respirators which includes a vaporizer arranged in a housing for evaporating water into the respiratory gas and for feeding the gas to be wetted through the housing while the water is heated and for subsequently providing an additional heating of the gas at the vicinity of the vaporizer in accordance with the temperature of the gas as it is measured at the mouthpiece connection to the patient.

DESCRIPTION OF THE PRIOR ART

During ventilation of the patient, the required moist and warm atmosphere must be maintained in the breathing passages. For this purpose, the inhaled air is wetted and warmed.

A known device to warm up and wet gases or gaseous mixtures for ventilation purposes is equipped with a water vaporizer chamber for the evaporation of water on the water surface. The water supply under visual control is poured into an externally heated tank. The tank forms an air space beneath a domed cover through which the breathing gas to be wetted is fed. An absorbent, material-coated metallic conductor device projects from the tank into the air space. The rising water is evaporated into the air space by the conductor device. Thereby, the air is heated to a temperature put out via the water and conductor device, which does not exceed the maximal temperature required for constant operation. A flexible synthetic tube leading to the patient is connected to the air space output as a delivery unit, which is provided internally with an electric resistance heating extending over its entire length. This heating is so adjusted that the temperature rise produced in the inhaled air equals or exceeds the temperature drop of the air on its way from humidifier unit output to the patient.

An undefined type of breathing gas overheating attained in this device is adapted to heat elimination conditions in the delivery unit. The housing-contained large air space is substantially fed into the clearance volumes of the entire ventilation system and effects its ventilation specific parameter in an undesirable manner. Because of the large water volume, an extended heatup time and sluggish control is produced. However, the water evaporation produced temperatures favor, rather than prevent, the transport of bacteria from the ambient air to the patient. Equipping the tube leading to the patient with a heater impairs its flexibility in conjunction with a simultaneous weight increase. Arranging electrical heaters in patient proximity represents a risk in failure cases, e.g., with wire break produced overheating temperatures there, which can be serious, specifically in connection with oxygen applications, see German Offenlegungschrift No. 2,032,421.

A gas wetter for breathing units is also known, and it includes a water vaporizer chamber for evaporating water on the water surface. The water in the vaporizer chamber is heated by a heater element arranged under the water surface. The breathing gas is carried through the vaporizer chamber and conducted thereover the water surface by deflector plates. It thereby absorbs the condensed water component from the water surface. With this gas wetter, the wetting and heating of the breathing gas takes place above a water surface. To obtain a sufficiently large water vapor volume, the evaporating surface must be large. This makes for large-dimensional humidifiers. The large volume produced in this way results in sluggish control. Bacterial growth is not forestalled because of the insufficiently increased water temperature. When the room temperature drops, more energy is fed to the heater element through controlling means so that the breathing gas in the wetting space is heated up more and enriched with water vapor. This results in an increased condensate development in the breathing air tube, see German Offenlegungschrift No. 2,240,659.

Another device for wetting breathing gases is known, wherein an electrically heated boiler cartridge projects into the breathing gas conductor wetting space. It is so enveloped by a perforated water conductor shell that, between both of them, an annular space is produced. The water is fed to the annular space by metering means and is spontaneously evaporated on the boiling temperature heated-up boiler cartridge. Steam is admitted through holes in the water conductor shell to the breathing gas, which is heated by steam and the flow in contact with the water conductor shell. Thus, in the further breathing gas conduction to the patient, condensation, even with the cooling effected in the breathing air tube, is substantially prevented. The high temperature of the boiler cartridge prevents a bacterial contamination of the breathing gas. The high heat input of the vaporizer device from the boiler cartridge and water conductor shell makes it difficult to control the breathing temperature on a short time basis. The degree of overheating of the breathing gas effective at the output of the device is not exactly defined and would have to be balanced up to the patient stage by a suitable balancing of air tube data, see German Pat. No. 2,516,496.9.

SUMMARY OF THE INVENTION

According to the invention, the vaporizer is equipped with a heating cartridge under the feed controlled water surface, which keeps the water boiling, and includes a mixer chamber above, to which a breathing gas feeder line and a breathing gas exit line are connected, and behind the vaporizer, there is a built-in overheater having a heater element controlled by a temperature sensor which is arranged just in front of the patient's mouthpiece connection to the respirator.

The advantages obtained by the invention are that it is possible to keep the volume small with boiling water. Practically, only the water volume to be evaporated must be fed in. The water vapor is admitted directly into the mixer chamber, and it is mixed there with the breathing gas conducted through the breathing gas feed line. The breathing gas is heated by way of the water vapor. Because of the constant water boiling temperature, there are no disturbing effects produced by any additional heating capacity, for example, from a vaporizer cartridge. Because of the small evaporation volume, the compressible volume remains low. Accordingly, a short time temperature control is feasible. Any condensation in the breathing gas feeder line is prevented in a safe manner by way of overheating the breathing gas. The moisture is controlled as a function of the temperature in front of the patient's mouth. Beyond that, safeguards are provided that the breathing gas temperature for the patient exactly matches the set one, that is, the desired level. It remains independent from the ambient temperature.

Accordingly, it is an object of the invention to provide a breathing gas humidifier for connection between a respirator and a patient which comprises a mixing chamber having a bottom connection to a float chamber for water which is filled to a selected level in the flow chamber and extends upwardly into the mixing chamber and which also has a top connection to the float chamber and which includes a respiratory gas breathing line which is adapted to be connected between the respirator and the patient and which includes the passage for the gas through the mixing chamber to a discharge which is adapted to extend to the patient's mouth and which further includes means for heating the gas in the mixing chamber and for providing a subsequent heating of the gas after it leaves the mixing chamber in accordance with a temperature which is sensed at the mouthpiece connection to the patient.

A further object of the invention is to provide a breathing gas humidifier which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

GENERAL DESCRIPTION OF THE PREFERRED EMBODIMENT

Figure 1:
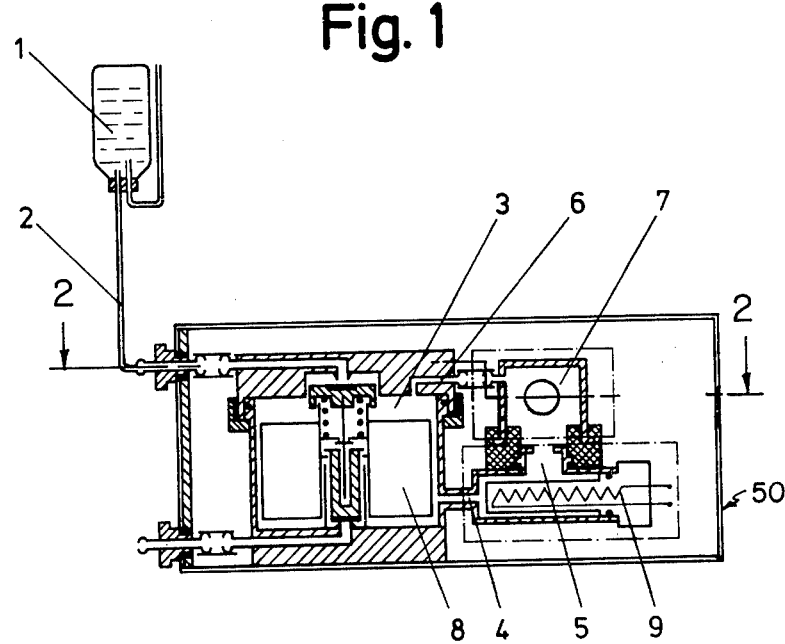
FIG. 1 is a transverse sectional view of a respiratory gas humidifier constructed in accordance with the invention.
Figure 2:
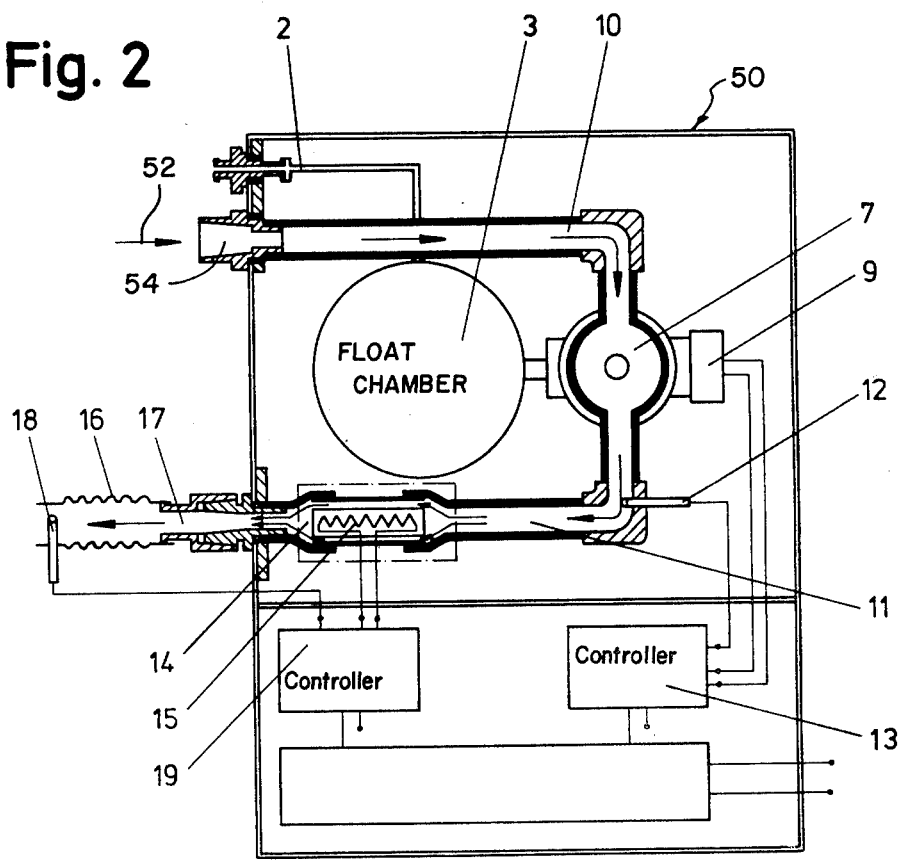
FIG. 2 is a section taken along the line 2—2 of FIG. 1.

Referring to the drawings in particular, the invention embodied therein, comprises a breathing gas humidifier, generally designated 50, which includes a housing defining a water and gas mixing chamber 7 which is connected by a bottom connection 4 to a float chamber 3 also defined by the housing which is adapted to be filled with water up to a predetermined level as determined by a float body 8. Sterilized water is added from a sterilized water supply 1 through a connecting line 2 into the top of the tank 3.

A top connection 6 is provided above water line level between the float chamber 3 and the mixing chamber 7. Respirator gas is circulated from a respirator (not shown) in the direction of the arrow 52 through an inlet 54 and a breathing gas feed line 10 which extends through the mixing chamber and has a discharge or gas exit portion 11 which is adapted to be connected at its outer end over an air tube 16 to a mouthpiece used by a patient (not shown).

The water to be evaporated is supplied from the sterilized water supply 1 into the float chamber 3 through connector line 2 and flows over into the vaporizer 5 via bore 4. Pressure compensator line 6 connects mixer chamber 7 to the empty space above float body 8. In both spaces, it prevents various gas pressures from affecting the water level control. heating cartridge 9 is built into vaporizer 5 which has a capacity of about 20 ml. The water is brought to a boil by feeding electric power into heating cartridge 9. The water vapor produced is admitted directly into mixer chamber 7.

The breathing gas is let into mixer chamber 7 by the breathing gas feed line 10 and let off again by the breathing gas exit line 11. By mixing with water vapor, the breathing gas is preferably heated to 35 degrees C. and is wetted to 100% relative humidity. Temperature sensor 12 monitors the output temperature from mixer chamber 7 and controls the power supply to heating cartridge 9 via controller 13.

The warmed-up and water vapor-saturated breathing gas from mixer chamber 7 is admitted into overheater 14 via breathing gas exit line 11, where it is heated to a higher temperature by a heater element 15. The relative humidity of the breathing gas thereby drops to values less than 100%. The temperature increase in overheater 14 is necessary because of heat dissipation in patient air tube 16. Some factors effecting this heat dissipation, among others, are the air tube geometry, the air tube material, the breathing gas flow and room temperature. The overheated breathing gas exits at bushing 17 from overheater 14 and is let into a patient air tube 16. On the way to the patient, it is cooled off again to the original temperature in breathing gas exit line 11, preferably 35° C., whereby, a 100% relative humidity level is then reached again. Temperature sensor 18 is connected near the mouthpiece end of air tube 16 and tests the patient connector temperature and controls the power supply to heater element 15 in overheater 14 through controller 19 and, in that way, insures the required breathing gas temperature and relative humidity.

While a specific embodiment of the invention has been shown and described in detail to illustrate the application of the principles of the invention, it will be understood that the invention may be embodied otherwise without departing from such principles.

What is claimed is:

1. A breathing gas humidifier for connection between a respirator and a patient, comprising a water and breathing gas mixture chamber, means for maintaining a predetermined level of water in said mixing chamber, a respiratory gas connection line having a first portion with one end including means connectable to a respirator and extending from said one end into said mixing chamber, said gas connection line having an opposite second portion extending out of said mixing chamber and having a second portion end, an air tube having one end connected to said second portion end and an opposite end including means connectable to said respirator, first heater means in said mixing chamber for heating the water therein to vaporize it and to permit it to be picked up by the breathing gas being passed over the water level in said mixing chamber through said gas connection line second portion, second heater means in said gas connection line second portion for overheating the breathing gas with vaporized water from said mixing chamber, temperature-sensing and control means connected to said first and second heater means, said means for maintaining a predetermined level of water in said mixing chamber including a float chamber, and means connected to said float chamber containing distilled water for supplying water to said float chamber, a float valve in said float chamber for closing the connection between said distilled water containing means and said float chamber when a predetermined level of water is reached in said float chamber, said mixing chamber comprising a lower vaporizer chamber of a size substantially smaller than said float chamber for containing a quantity of water substantially smaller than a quantity of water in said float chamber and an upper water vapor and breathing gas mixing chamber, said first heater means disposed in said lower vaporizer chamber, said lower vaporizer chamber being sufficiently small so that said first heater means vaporizes substantially all the water therein, and a top conduit connection connected between said upper water vapor and breathing air mixing chamber and the top of said float chamber whereby the predetermined level of water in said float chamber is maintained in said vaporizer chamber, said temperature sensing and control means controlling said first heater means for heating and vaporizing said smaller quantity of water thereby when mixed with said breathing gas in said upper chamber said breathing gas is maintained at about 35° C. and at a humidity level of 100%, and controlling said second heater means for overheating said breathing gas from said upper water vapor and breathing gas mixing chamber to at least partially compensate for cooling of the breathing gas with vaporized water in said gas connecting line second portion and said air tube to thereby maintain said breathing gas at about 35° C. having a humidity level of 100%.

2. A breathing gas humidifier, according to claim 1, wherein said temperature sensing and control means includes a temperature sensor adjacent said air tube opposite end for sensing the temperature of the breathing gas with vaporized water and means for regulating said second heater in accordance with the temperature sensed to maintain said breathing gas at about 35° C. and at a humidity level of 100% a further temperature sensor in said second portion of said gas connection line adjacent said mixing chamber for sensing the temperature in the breathing gas with vaporized water, and means connected to said further temperature sensor and to said first heater for controlling said first heater to sufficiently vaporize the water in said mixing chamber and thereby when mixed with said breathing gas in said upper chamber, said breathing gas is maintained at about 35° C. and at a humidity level of 100%.

* * * * *